United States Patent [19]

Davis et al.

[11] 3,950,535

[45] Apr. 13, 1976

[54] CYANOBENZYL CYCLOPROPANE CARBOXYLATES

[75] Inventors: Royston H. Davis, Rainham; Robert J. G. Searle, Rodmersham Green, both of England

[73] Assignee: Shell Oil Company, Houston, Tex.

[22] Filed: Sept. 30, 1974

[21] Appl. No.: 510,197

[30] Foreign Application Priority Data

Oct. 8, 1973    United Kingdom............... 46926/73

[52] U.S. Cl. ........ 424/304; 260/465 D; 260/468 G; 424/305
[51] Int. Cl.² .................. A01N 9/20; C07C 121/66
[58] Field of Search.................. 260/465 D; 424/304

[56] References Cited
UNITED STATES PATENTS 3,835,176   9/1974   Matsuo et al. ...................... 260/465

Primary Examiner—Lewis Gotts
Assistant Examiner—Dolph H. Torrence

[57] ABSTRACT

Cyclopropane derivatives of the formula

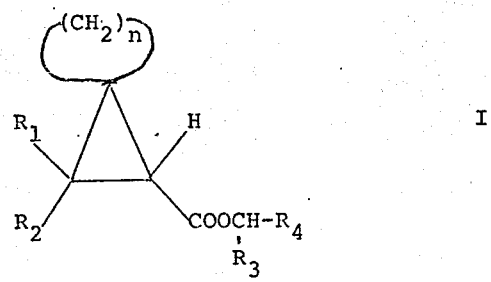

wherein $R_1$ and $R_2$ are alkyl; $R_3$ is hydrogen, alkynyl or cyano; $R_4$ is optionally substituted phenyl and in is an integer of 2 to 5, are useful as pesticides.

7 Claims, No Drawings

CYANOBENZYL CYCLOPROPANE CARBOXYLATES

FIELD OF THE INVENTION

This invention relates to novel cyclopropane derivatives which exhibit pesticidal, expecially insecticidal and acaricidal properties.

SUMMARY OF THE INVENTION

Accordingly, the present invention provides cyclopropane derivatives having the general formula

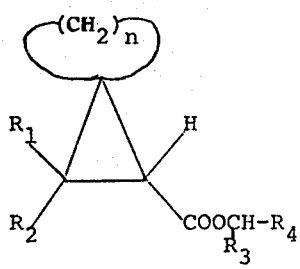

wherein $R_1$ and $R_2$ each represents an alkyl group; $R_3$ represents a hydrogen atom or an alkynyl or cyano group; $R_4$ represents an optionally substituted phenyl, suitable substituents being halogen, phenoxy or benzyl; and $n$ is an integer from 2 to 5.

More particularly, the cyclopropane derivatives are those of formula I, wherein $R_1$ and $R_2$ each represents an alkyl group of 1–6 carbon atoms, especially a methyl group; $R_3$ represents a hydrogen atom, cyano group or allkynyl of 2–4 carbon atoms, especially an ethynyl group; and $R_4$ represents a phenyl group optionally substituted by one or more halogens, that is, one or more chlorine, one or more bromine or one or more fluorine atoms or a phenoxy or benzyl group.

Preferred cyclopropane derivatives are those of formula I, wherein $R_1$ and $R_2$ are methyl; $R_3$ is a hydrogen atom or cyano group; and $R_4$ is phenyl substituted by five chlorines, or by a phenoxy group.

Particularly preferred cyclopropane derivatives are 3-phenoxybenzyl 2,2-dimethyl-3-spirocyclobutane-cyclopropane carboxylate, 3-phenoxy-alpha-cyanobenzyl 2,2-dimethyl-3-spirocyclobutane-cyclopropane carboxylate and 3-phenoxybenzyl 2,2-dimethyl-3-spirocyclohexane-cyclopropane carboxylate.

The cyclopropane derivatives of the invention may be prepared by a process which comprises reacting a compound of formula:

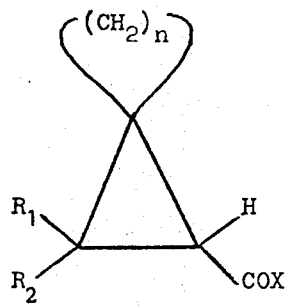

with a compound of formula:

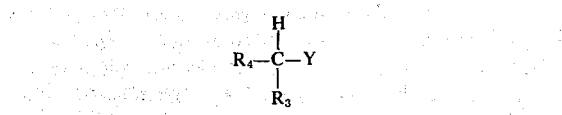

wherein one of the groups X and Y represents a halogen atom, suitably a chlorine or bromine atom, and the other represents a hydroxyl group. The reaction is preferably carried out in the presence of a hydrogen halide acceptor, for example a tertiary amine such as triethylamine, and in an organic solvent such as ether.

As mentioned above the cyclopropane derivatives of the invention are of interest as pesticides and the invention therefore includes pesticidal compositions comprising a carrier and/or a surface-active agent together with a cyclopropane derivative of formula I. Likewise the invention also includes a method of combating insect or acarid pests at a locus which comprises applying to the locus a cyclopropane derivative or composition of the invention.

The term 'carrier' as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the compositions of the invention, and suitable examples of these are to be found, for example, in British patent specification No. 1,232,930.

The compositions of the invention may be formulated as wettable powders, dusts, granules, solutions, emulsifiable concentrates, emulsions, suspension concentrates or aerosols. Wettable powders are usually compounded to contain 25, 50 or 75%w of toxicant and usually contain, in addition to solid carrier, 3–10%w of a dispersing agent and, where necessary, 0–10%w of stabilizer(s) and/or other additives, such as penetrants or stickers.

Dusts are usually formulated as a dust concentrate having a similar composition to that of a wettable powder but without a dispersant, and are diluted in the field with further solid carrier to give a composition usually containing ½–10%w of toxicant. Granules are usually prepared to have a size between 10 and 100 BS mesh (1.676–0.152 mm), and may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent and, when necessary, co-solvent, 10–50%w/v toxicant, 2–20% w/v emulsifiers and 0–20% w/v of appropriate additives such as stabilizers, penetrants and corrosion inhibitors. Suspension concentrates are compounded so as to obtain a stable, nonsedimenting, flowable product and usually contain 10–75%w toxicant, 0.5–15%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, especially insecticidal, acaricidal, herbicidal or fungicidal properties.

The invention is further illustrated in the following Examples.

EXAMPLE I

3-Phenoxybenzyl
2,2-dimethyl-3-spirocyclobutane-cyclopropane carboxylate 2,2-Dimethyl-3-spirocyclobutane-cyclopropane carboxylic acid (1.5 g), 3-phenoxybenzyl bromide (2.6 g) and triethylamine (1.00 g) in toluene (50 ml) were heated together under reflux for 1.5 hours. The solvent was then removed under reduced pressure and the residue was purified by chromatography on silica gel using a 1:20 mixture of ether in hexane as eluant. The required product was obtained as an oil.

Analysis Calculated for $C_{22}H_{24}O_3$: C 78.5; H 7.2%; Found: C 78.3; H 7.2%.

EXAMPLE II

3-Phenoxy-alpha-ethynylbenzyl
2,2-dimethyl-3-spirocyclobutane-cyclopropane carboxylate 2,2-Dimethyl-3-spirocyclobutane-cyclopropane carboxylic acid (0.5 g) was converted to its acid chloride by refluxing with thionyl chloride (2 ml) in benzene (10 ml) for 2 hours. The acid chloride, 3-phenoxy-alpha-ethynylbenzyl alcohol (0.9 g) and triethylamine (0.5 g) were then stirred together in benzene (50 ml) for 24 hours. The reaction mixture was worked up in a similar manner to that described in Example I to give the desired product as an oil.

Analysis Calculated for $C_{24}H_{24}O_3$: C 79.15; H 6.7%; Found: C 79.4; H 6.8%.

EXAMPLE III

3-Phenoxybenzyl
2,2-dimethyl-3-spirocyclopropane-cyclopropane carboxylate 2,2-Dimethyl-3-spirocyclopropane-cyclopropane carboxylic acid (0.7 g), 3-phenoxybenzylbromide (1.3 g) and potassium carbonate (0.35 g) in acetone (40 ml) were stirred together at room temperature for 24 hours. The solvent was removed and the residue purified by chromatography using a 1:9 mixture of methylene dichloride in carbon tetrachloride as eluant. The required product was obtained as an oil, $n_D^{22}$ 1.5499.

Analysis Calculated for $C_{21}H_{22}O_3$: C 78.2; H 6.9%; Found: C 78.0; H 6.8%.

EXAMPLE IV

3-Phenoxy-alpha-cyanobenzyl
2,2-dimethyl-3-spirocyclopropane-cyclopropane carboxylate 2,2-Dimethyl-3-spirocyclopropane-cyclopropane carboxylic acid (1.0 g), 3-phenoxy-alpha-cyanobenzylbromide (1.9 g) and potassium carbonate (0.5 g) in acetone (100 ml) were stirred together for 24 hours at 20°C. The mixture was filtered and after evaporation of the filtrate the pale yellow oil was purified by chromatography on silica gel using a 1:1 mixture of chloroform and hexane as eluant. The required product was obtained as an oil, $n_D^{19.5}$ 1.5484.

Analysis Calculated for $C_{22}H_{21}O_3N$: C 76.1; H 6.1; N 4.0%; Found: C 75.5; H, 6.7; N 3.6%.

EXAMPLE V

3-Benzylbenzyl
2,2-dimethyl-3-spirocyclopropane-cyclopropane carboxylate 2,2-Dimethyl-3-spirocyclopropane-cyclopropane carboxylic acid (1.0 g), 3-benzylbenzyl chloride (1.0 g) and potassium carbonate (0.5 g) in acetone (50 ml) were stirred and refluxed for 48 hours. The solvent was removed and the residue purified by chromatography on silica gel using a 1:1 mixture of chloroform/hexane as eluant. The required product was obtained as an oil, $n_D^{19}$ 1.5469.

Analysis Calculated for $C_{22}H_{24}O_2$: C 82.5; H 7.6%; Found: C 82.3; H 7.4%.

EXAMPLE VI

Following procedures similar to those of Examples I and II further compounds were prepared whose physical characteristics and analyses are given in Table I.

EXAMPLE VII

Insecticidal and acaricidal activity

The insecticidal and acaricidal activity of the compounds of the invention was tested as follows:

I. A 1.0% by weight solution in acetone of the compound to be tested was prepared, and taken up in a micrometer syringe. Two to 3-day old adult female house flies (*Musca domestica*) were anaesthetized with carbon dioxide, and 1 µl drop of the test solution was brushed off on the ventral abdomen of each, 20 flies being treated. The treated flies were held for 24 hours in glass jars, each containing a little granulated sugar as food for the flies, and the percentage of dead and moribund individuals was then recorded.

TABLE I

| Compound | Ref. Index or m.p. | Analysis | |
|---|---|---|---|
| 3-phenoxybenzyl 2,2-dimethyl-3-spirocyclohexanecyclopropane carboxylate | n.d. | Calculated for $C_{24}H_{28}O_3$: Found: | C 79.1; H 7.7% C 78.7; H 7.7% |
| 3-phenoxy-alpha-cyanobenzyl 2,2-dimethyl-3-spirocyclobutane-cyclopropane carboxylate | $n_D^{17}=$ 1.5529 | Calculated for $C_{23}H_{23}NO_3$: Found: | C 76.4; H 6.4; N 3.9% C 76.4; H 6.6; N 3.8% |

TABLE I-continued

| Compound | Ref. Index or m.p. | Analysis | |
|---|---|---|---|
| pentachlorobenzyl 2,2-dimethyl-3-spirocyclopropane-cyclopropane carboxylate | m.p. 81–83°C | Calculated for $C_{15}H_{13}O_2Cl_5$: Found: | C 44.8; H 3.2% C 45.8; H 3.2% | n.d. = not determined

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under-surface of the leaf with the above formulation. Spraying was effected with a spraying machine delivering 450 liters per hectare, the plants passing under the spray on a moving belt. Ten adult 1–2 week-old mustard beetles (Phaedon cochleariae) were placed on the sprayed leaf of each turnip plant and 10 apterous (6-day-old) vetch aphids (Megoura viciae) were placed on the sprayed leaf of each broad bean plant. The plants were then enclosed in glass cylinders fitted at one end with a muslin cap. Mortality counts were made after 24 hours.

III. In tests against glass house spider mites (Tetranychus urticae), leaf discs cut from French bean plants were sprayed in the manner described under II. One hour after spraying, the discs were inoculated with 10 adult mites. Mortality counts were made 24 hours after inoculation.

IV. In tests against large white butterfly larvae (Pieris brassicae), leaf discs cut from cabbage leaves were sprayed in the manner described under II. Ten 3rd instar (8–10 day-old) larvae were placed on the discs within petri-dish pairs. Mortality counts were again made 24 hours after inoculation.

The results of these tests are shown in Table II, in which A denotes complete kill, B some kill and C no kill of the test species.

TABLE II

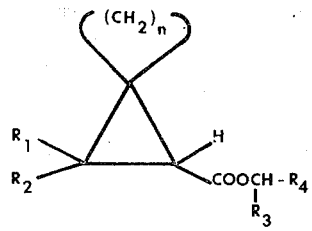

| Compound | | | | | Pesticidal activity | | | | |
|---|---|---|---|---|---|---|---|---|---|
| $R_1$ | $R_2$ | $R_3$ | $R_4$ | n | M.domestica | P.cochleariae | P.brassicae | M.viciae | T.urticae |
| $CH_3$ | $CH_3$ | H | 3-phenoxyphenyl | 3 | A | A | A | A | B |
| $CH_3$ | $CH_3$ | H | 3-phenoxyphenyl | 5 | A | B | A | A | B |
| $CH_3$ | $CH_3$ | H | 3-phenoxyphenyl | 2 | A | C | A* | B | B |
| $CH_3$ | $CH_3$ | CN | 3-phenoxyphenyl | 2 | A | — | — | — | — |
| $CH_3$ | $CH_3$ | C CH | 3-phenoxyphenyl | 3 | A | C | — | A | B |
| $CH_3$ | $CH_3$ | CN | 3-phenoxyphenyl | 3 | A | B | A* | A | A |
| $CH_3$ | $CH_3$ | H | pentachlorophenyl | 2 | A | C | A* | B | B |
| $CH_3$ | $CH_3$ | H | 3-benzylbenzyl | 2 | A | C | A* | B | B |

*Results obtained in tests against rice swarming caterpillars (Spodoptera litoralis)

What we claim is:

1. Cyclopropane carboxylate derivatives of the formula:

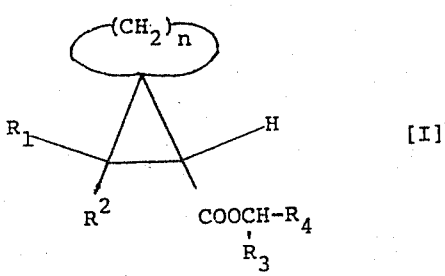

wherein $R_1$ and $R_2$ each represents an alkyl group; $R_3$ represents a cyano group; $R_4$ represents a phenyl group optionally substituted by halogen, phenoxy or benzyl; and n is an integer from 2 to 5.

2. A cyclopropane carboxylate derivative as claimed in claim 1, wherein $R_1$ and $R_2$ each represents an alkyl group of 1–6 carbon atoms, $R_3$ represents a cyano group and $R_4$ represents a phenyl group optionally substituted by one or more halogen atoms or by phenoxy or benzyl group.

3. A cyclopropane carboxylate derivative as claimed in claim 2, wherein $R_1$ and $R_2$ each represents a methyl group, $R_3$ represents a cyano group and $R_4$ represents a phenoxy-substituted phenyl group or a pentachlorophenyl group.

4. 3-Phenoxy-alpha-cyanobenzyl 2,2-dimethyl-3-spirocyclobutane-cyclopropane carboxylate.

5. 3-Phenoxy-alpha-cyanobenzyl 2,2-dimethyl-3-spirocyclopropane-cyclopropane carboxylate.

6. Pesticidal compositions comprising a carrier and/or a surface-active agent, together with, as active ingredient, a pesticidally effective amount of a cyclopropane carboxylate derivative as claimed in claim 1.

7. A method of combating insect and/or acarid pests at a locus which comprises applying to the locus a pesticidally active amount of a cyclopropane carboxylate derivative as claimed in claim 1 or a composition thereof.

* * * * *